(12) United States Patent
Kelly

(10) Patent No.: US 6,696,071 B2
(45) Date of Patent: Feb. 24, 2004

(54) PRE-COITAL AND POST-COITAL RINSE WITH ANTI-VIRAL AND SKIN-PROTECTIVE ZINC SALTS

(76) Inventor: Patrick D. Kelly, 11939 Manchester #403, St. Louis, MO (US) 63131

( * ) Notice: Subject to any disclaimer, the term of this patent is extended or adjusted under 35 U.S.C. 154(b) by 0 days.

(21) Appl. No.: 10/001,045

(22) Filed: Nov. 27, 2001

(65) Prior Publication Data

US 2003/0099720 A1 May 29, 2003

(51) Int. Cl.$^7$ ............... A01N 25/04; A01N 59/16; A61F 13/02; A61F 9/02; A61K 33/32
(52) U.S. Cl. ............... 424/405; 424/430; 424/433; 424/436; 424/641; 424/642
(58) Field of Search ............... 424/405, 430, 424/433, 436, 641, 642

(56) References Cited

U.S. PATENT DOCUMENTS 5,208,031 A * 5/1993 Kelly ............... 424/412

\* cited by examiner

*Primary Examiner*—Carlos A. Azpuru
(74) *Attorney, Agent, or Firm*—Patrick D. Kelly

(57) ABSTRACT

An aqueous douche or enema is disclosed, containing a water-soluble zinc salt at an anti-viral concentration, designed for use shortly before and/or shortly after intercourse. Unlike a lubricant for use during intercourse, this type of rinsing liquid will not contain glycerine or similar lubricating components, and will be designed to not leave behind a film-type residue. However, this type of "pericoital" rinse (i.e., intended for pre-coital or post-coital use) will leave behind positively-charged zinc ions. Due to electrostatic attraction, these $Zn^{++}$ ions will cling to negatively-charged canyons and other "binding sites" in proteins that are exposed and accessible on the surfaces of cells and virus particles. The binding of $Zn^{++}$ ions to negatively-charged sites in these surface proteins will alter and disrupt the ability of viruses (including herpes and HIV) to bind to and infect human cells. Accordingly, this type of rinse can reduce the risk of infection by sexually transmitted viruses, in a person who is not previously infected. In addition, due to the skin-protective properties of zinc, a pericoital rinse containing a water-soluble zinc salt can help accelerate the healing and closure of microabrasions, lesions, and other breaches or deficits in genital skin or mucous membranes, thereby further decreasing the risk of viral infections following intercourse.

12 Claims, No Drawings

PRE-COITAL AND POST-COITAL RINSE WITH ANTI-VIRAL AND SKIN-PROTECTIVE ZINC SALTS

BACKGROUND OF THE INVENTION

This invention relates to biochemistry, and to anti-viral agents for use as preventive agents, to reduce the risk that a previously uninfected person will become infected by sexually-transmitted viruses (such as genital herpes, HIV/AIDS, hepatitis, or papilloma viruses) or other microbial diseases (such as syphilis, gonorrhea, or chlamydia).

The anti-viral activity of zinc salts and zinc ions, when applied topically to mucous membranes inside the body, is discussed in a number of prior patents issued to George Eby, involving lozenges taken by mouth (e.g., U.S. Pat. Nos. 4,503,070 and 5,409,905).

Various additional US patents involving the use of zinc salts in genital lubricants, for use during sexual intercourse, have been issued to Patrick Kelly, the same inventor herein. Those patents include U.S. Pat. Nos. 5,208,031 (May 1993), 5,482,053 (January 1996), 5,624,675 (April 1997), and 5,980,477 (November 1999). The contents of those patents are incorporated herein, as though set forth in full. Published articles describing the inhibition of herpes viruses by zinc salts include Eby & Halcomb 1985, Kumel et al 1990, and Arens & Travis 2000.

Novick et al 1996 proposes a specific molecular mechanism that would allow zinc to exert a substantial anti-viral effect, outside of cells and membranes. In this mechanism, positively charged zinc ions ($Zn++$), which are released when a water-soluble zinc salt is dissolved in water, are attracted to negatively-charged canyons, in the surface proteins that are present on the surfaces of virus particles and cells. Since opposites attract, the positively-charged zinc ions settle into the negatively-charged protein canyons, and occupy those canyons.

This disrupts and alters the binding conformation and affinity of the surface proteins, in a manner comparable to shoving a toothpick or paperclip into a keyhole. On a visible level, as long as a foreign object remains jammed in a keyhole, it will be impossible to fit the real key into that keyhole. On a molecular level, as long as positively-charged zinc ions occupy and disrupt negatively-charged canyons in the surface proteins that enable virus particles to bind to certain types of cells, virus particles that have been exposed to an adequate concentration of zinc ions will not be able to bind to and infect cells having the surface proteins that are normally targeted by the virus particles.

Another potential mechanism that may help explain zinc's anti-viral activity should also be noted. Zinc ions are known to form relatively stable and strong crosslinking bonds with cysteine and histidine residues, in proteins. In nature, these crosslinking bonds normally cause two different strands of a single protein to become bound to each other, and they are highly important in establishing and stabilizing the three-dimensional conformations of many types of proteins, including so-called "zinc finger proteins".

In a situation involving a lubricant or rinse that contains zinc ions in a concentration that is thousands of times greater than can be established in natural biological fluids, the same types of crosslinking bonds, made in very large numbers by a huge surplus of free zinc ions, can collectively provide sufficient strength to randomly bind viral particles to each other, and to proteins on the surfaces of dead and dying ("pyknotic") cells that are being sloughed off continuously by the epidermal and epithelial membranes of the penis, vagina, and rectal cavity. This can effectively prevent the entangled virus particles from infecting viable cells and establishing an active infection.

In addition, zinc is known to have skin-protective and mild wound-healing properties. Zinc compounds such as zinc oxide and zinc acetate are present in hundreds of ointments and creams, including nearly every type of ointment sold and used today for treating diaper rash, bedsores, etc. Published articles that describe the activity of zinc in promoting wound healing and skin closure, and in stabilizing cell membranes and multi-cellular membranes, include Chvapil 1973 and 1976, Agren 1990, Bray & Bettger 1990, Hennig et al 1992, Kaszuba & Hunt 1990, Mahadevan, et al 1990, Pasternak 1990, Pasternak et al 1992, and Hennig et al 1992. In addition, Chvapil et al 1978 and 1980 reported that when certain zinc salts were added to certain contraceptive products, the zinc seemed to reduce detectable signs of irritation and inflammation caused by the other agents.

Williams 1980 indicated that zinc salts had mild contraceptive activity in rabbits. Although zinc's level of contraceptive potency in that report was insufficient to support commercialization and public use, it also reportedly increased the contraceptive potency of nonoxynol, a widely used spermicide, in those tests.

Despite those steps forward, various problems have blocked any actual public or commercial use of zinc in genital lubricants. As of the filing date of this application, in November 2001, there are no genital lubricant products (either in a stand-alone liquid or gel, or pre-packaged with a condom) which are on the market and available to the public, which contain a zinc salt as an anti-viral additive. One of the major problems which has hindered the licensing and commercialization of genital lubricants with zinc salts has been an unending dispute over the efficacy of zinc lozenges; for every report which describes a positive result, another report describing a negative result has also appeared. In addition, for various reasons (which seem to center around profit potentials, unproven technology, and the difficulty and expense of carrying out human clinical trials of a size needed to establish clear evidence that is strong enough to satisfy the U.S. Food and Drug Administration, and comparable agencies in other countries), the major pharmaceutical companies of the world have refused to make serious commitments to funding research on any types of topical genital microbicides. This assertion can be borne out by various news articles and industry surveys distributed by the Alliance for Microbicide Development (Silver Spring, Md.; www.microbicides.org), and other organizations working on topical microbicides intended for use on the genitals, such as The Population Council (New York City; www.popcouncil.org) and CONRAD (Contraceptive Research and Development; Arlington, Va.; www.conrad.org)

Accordingly, one object of this current invention is to disclose a novel formulation for using a rinse-type formulation containing a suitable zinc salt, either shortly before coitus or shortly following coitus, to reduce the risk of infection by sexually transmitted viruses.

Another object of this patent application is to further expand the set of patent rights which can be used to help support and justify funding for the scientific research that will be necessary to establish a clear scientific consensus on whether a suitable zinc compound, in a topical formulation applied to one or more genital surfaces, is indeed a safe, effective, and useful anti-viral agent for reducing the risk of infection by sexually transmitted viruses.

SUMMARY OF THE INVENTION

This invention discloses the use of an aqueous rinsing liquid which contains a water-soluble zinc salt at an anti-viral viral concentration, and which is designed to be used as a genital rinsing and cleansing agent, shortly before and/or shortly after intercourse, comparable to a douche or enema. Unlike a lubricant gel or liquid, which will contain a lubricating agent with an affinity for skin (such as glycerin), this type of rinsing liquid will be designed to not leave behind any substantial residue, other than zinc ions. This type of "peri-coital" rinse (i.e., intended for pre-coital or post-coital use) will leave behind a residue of positively-charged zinc ions. Due to electrostatic attraction, these $Zn^{++}$ ions will cling to negatively-charged canyons and other negative "binding sites" in proteins that are exposed and accessible on the surfaces of cells or virus particles. The binding of $Zn^{++}$ ions to negatively-charged binding sites in these surface proteins will alter and disrupt the ability of viruses (including herpes and HIV, and probably hepatitis and papilloma viruses as well) to bind to and infect human cells. Accordingly, a peri-coital rinse containing a water-soluble zinc salt can reduce the risk of infection, by sexually transmitted viruses, in a person who is not previously infected.

In addition, due to the skin-healing properties of zinc, a zinc-containing peri-coital rinse can also help promote and accelerate the healing and closure of microabrasions, lesions, and other breaches or deficits in genital skin or mucous membranes. Since intact skin plays a major role in fighting off infections, genital abrasions and lesions can greatly increase the risk of viral and other infections.

DESCRIPTION OF THE PREFERRED EMBODIMENTS

As summarized above, this invention discloses the use of an aqueous liquid which is designed for use as a vaginal or rectal rinse, in a form directly comparable to a douche or enema. This rinse formulation contains a water-soluble zinc salt, which will release zinc ions at an anti-viral concentration. By using this type of rinse as a douche or enema, shortly before and/or shortly after sexual intercourse, the anti-viral zinc ions can reduce the risk of a previously uninfected person becoming infected by sexually transmitted viruses, such as herpes viruses, human immunodeficiency viruses, hepatitis viruses, and papilloma viruses. This type of rinse is also believed to be able to reduce the risk of infection by other types of sexually transmitted diseases as well, including syphilis, gonorrhea, and chlamydia.

To provide maximal protection, this type of zinc-containing douche or enema should be used both before and after each act of intercourse in which there is a significant risk of transmission of a sexually transmitted microbe. However, a substantial degree of protection can be provided by a single use, either before or after intercourse. In particular, a recent report (Vernazza 2001) has indicated that HIV particles are actively shed into vaginal fluids, even among women who are taking anti-HIV drugs that suppress viral concentrations in the blood to very low or even undetectable levels. This appears to suggest that, if someone has only a limited supply of an anti-viral rinse, use prior to intercourse may be more beneficial than use after intercourse. However, this will need to be confirmed by actual tests, and if only a single rinsing step is planned, it should be done either very soon before or very soon after intercourse.

Preferably, an anti-viral zinc rinse as disclosed herein should be used in conjunction with a condom, during intercourse in which a significant risk of HIV, herpes, or other viral transmission exists; however, since that doesn't always happen, this type of rinse can be used regardless of whether a condom is also used, to provide at least some increased level of protection.

A zinc-containing douche or enema as disclosed herein must be suited in all respects for repeated periodic use, such as several times each week, or on a daily basis. As such, it must be free of any compounds that would inflict gradual accumulating damage, or an accumulating risk of carcinogenicity or other toxicity, when used repeatedly, such as before and after each act of intercourse.

As used herein, the term "rinse" excludes "genital lubricants". As used herein, a "genital lubricant" is a friction-reducing formulation that is effective, desirable, and comfortable, when used topically, as a lubricant, during intercourse. As such, a genital lubricant (as that term is used herein) must contain at least one agent that is conventionally used as a lubricating agent. Glycerin (also called glycerine, glycerol, 1,2,3-propanetriol, and trihydroxypropane) and certain types of polyethylene glycol (PEG), such as PEG 200 or PEG 400 (the numbers indicate different molecular weight averages) are widely used as lubricating agents in topical formulations. Various other polymers (such as polypropylene glycol, polyisobutene, and polyoxyethylene) and behenic acid and behenyl alcohol are also used as lubricants in cosmetics and other formulations that contact the skin. In addition, some sugar-alcohols such as sorbitol, and some silicon compounds such as polydimethyl-siloxane, are also used as skin and/or genital lubricants. When rubbed between two fingers, it quickly becomes clear that any of these agents will impart a "slippery" feel to the skin, in a manner which easily surpasses the lubricating traits of water.

As part of its ability to impart sustained lubrication and comfort throughout a complete act of intercourse, an effective genital lubricant must have an affinity for skin. This is evidenced by two distinct but consistent and overlapping factors. First, a lubricant will remain on the skin, as a fairly consistent and uniform coating, for a substantially longer period of time than water, or a rinsing formulation that does not contain a lubricant. The second factor is this: most types of lubricants, if allowed to dry on the skin without being wiped off, will leave a residue, usually in the form of a film, which often goes through a somewhat adherent "sticky" phase, and which may remain sticky until washed off.

By contrast, a genital "rinse", when defined in a manner that explicitly excludes lubricating ingredients such as glycerin, polyethylene glycol, etc., will not create the type of coating layer and/or sticky residue that a lubricant will create. A rinse should, instead, behave in a manner which is closer or even directly comparable to the performance of plain water, or salt water, when used to wash off the skin. In the same way that water can be used to rinse off something, a rinse, as defined herein, can also wash things off, and wash things out, in an effective manner that will not leave a sticky residue or film caused by an ingredient in the rinse.

However, this does not imply that a rinse will be able to wash off a pre-existing oily layer. Just as plain water, when applied gently to a sensitive area of skin, will not cleanly wash off an oily layer, neither should a rinse. A rinse generally should not act as a "stripping" agent, and should not contain substantial quantities of solvents, detergents, or surfactants that are designed to break down oils, lipids, or other hydrophobic compounds that are normally present on skin surfaces.

Nevertheless, it should be recognized that a rinse can contain a moisturizing ingredient, if desired, to counteract the astringent effects of nearly all zinc salts. Moisturizing agents which do not function effectively as lubricants are widely used in, for example, hand and face lotions and cosmetics which are non-oily, and which are designed to generate a clean and non-greasy feeling when used. As just one example, aloe vera gel is widely used as a moisturizing agent, but it would not perform adequately as a lubricating agent, if added to a genital lubricant. Various other such moisturizing ingredients are known to those who manufacture lotions and cosmetics, and may be incorporated if desired into a rinse formulation as disclosed herein, at appropriate concentrations (which in most cases are likely to be in the range of about 0.1 to 5%, by weight).

If desired, a rinse (as defined herein) may be labelled or otherwise regarded or presented as a rinse, douche, and/or enema formulation. The terms "douche" and "enema" are used in laymen's terms throughout this application; a "douche" as used herein is a liquid which is used to rinse out the vaginal cavity, while an "enema" as used herein is a liquid which is used to rinse out the rectal cavity. Unless otherwise noted, the term "rinse" refers to a liquid which can perform at least one and possibly both functions. Because preferred formulations for enemas and douches do not differ greatly, an anti-viral zinc rinse as disclosed herein may be suitable for either cavity, and preferred formulations should indeed be suited for either cavity.

It should be noted that the anti-viral zinc rinses disclosed herein are intended for rinsing out the vaginal and/or rectal cavities, and not the mouth. Some types of mouthwashes contain small quantities of zinc salts, mainly in the form of zinc chloride. Accordingly, although it is highly doubtful that such mouthwashes contain enough zinc to function effectively as an anti-viral agent, nevertheless, any mouthwashes or other formulations designed for oral use are excluded from coverage or consideration herein. This invention relates solely to products that are labelled or otherwise clearly intended to include vaginal and/or rectal use.

Preferred formulations for a zinc-containing rinse as disclosed herein can be based on formulations already in widespread use for douches and enemas. The compositions for such preparations are well-known to companies that market them, or can be determined through simple chemical analysis. However, if any such composition contains an ingredient that would act as a "chelating" agent for zinc ions, the chelating agent should be removed, and replaced if necessary by a similar agent that does not have chelating properties. As is known to chemists, chelating relates to a molecular binding reaction, wherein a chelating molecule binds to a certain atom or molecule with a tightness or avidity that effectively sequesters and inactivates the bound atom or molecule. As just one example, Vitamin C (ascorbic acid) tends to inactivate zinc ions, by binding to them. Accordingly, Vitamin C should not be included as an ingredient in an anti-viral zinc rinse as disclosed herein.

Rinse formulations as disclosed herein can be sold in fully hydrated form, if desired. Alternately, to reduce bulk, shipping costs, and the risk of storage and leakage problems, and to increase their shelf life, they can be sold as powders or concentrates, which can be converted into rinse formulas by dissolving them in water. They can be packaged in any desired manner, such as in a disposable squeeze bottle with a nozzle, if desired.

To maximize anti-viral efficacy when used before intercourse (i.e., precoital or pre-coital), a zinc-containing rinse preferably should be used a reasonable and relatively short period of time before intercourse commences, such as within an hour or possibly two hours before intercourse begins. In general, it is assumed that a rinsing step, using a zinc-containing douche or enema, is likely to have some significant beneficial effect, if carried out at any time within roughly 12 hours (and possibly more) prior to intercourse. However, since any viral load in an infected person will tend to return and build up gradually, over a span that can be measured in hours, and since any protective residual zinc ion concentrations that remain on accessible vaginal or rectal surfaces will gradually be absorbed and dissipated over time, a relatively short delay (such as only an hour, or less) before intercourse will provide a better margin of safety and protection than a longer delay (such as more than two hours). Accordingly, as a compromise which is intended to reasonably define and delimit phrases such as "before intercourse" or "prior to intercourse" in the claims, use of a rinse as disclosed herein within a period of up to 6 hours, prior to commencing intercourse, is deemed to be use "prior to intercourse" as covered by the claims below.

Since zinc salts tend to have an astringent effect, a precoital rinse can be followed by application of a moisturizing and/or lubricating compound (various vaginal moisturizers are well-known in the art). If desired, a moisturizer and/or lubricant containing a water-soluble zinc salt can be used, for greater anti-viral efficacy.

To maximize anti-viral efficacy when used after intercourse (i.e., postcoital or post-coital), a zinc-containing rinse preferably should be used within about 10 to 15 minutes after ejaculation. This shorter time limitation is based on data reported in Zacharopoulos et al 1992, Phillips & Bourinbaiar 1992, and Pearce-Pratt & Phillips 1993, which indicate that within about 15 minutes, HIV-infected lymphocytes commence a cellular process in which infected cells, rather than free virus particles, begin binding to uninfected epithelial cells, and begin shoving large numbers of HIV particles or genomes at and into the epithelial cells. Accordingly, use of a zinc-containing rinse within about 15 minutes or less after ejaculation is preferable, since it can reduce the risk of that type of cell-to-cell infection process.

However, since the 15 minute period observed in those tests was based on various parameters and conditions (including high-titer viral concentrations) that were designed to facilitate easily observable tests with clear outcomes, it is not believed that a 15 minute delay is a rigid boundary line, beyond which using an anti-viral zinc rinse would be a wasted effort. Instead, it is believed and assumed that post-coital use of a rinse at any time up to roughly 12 hours after intercourse may be able to significantly reduce the risk of infection. Accordingly, as above, a six-hour period following ejaculation is used as a compromise which is intended to reasonably define and delimit phrases such as "after intercourse" or "following intercourse" in the claims. Use of an anti-viral zinc rinse as disclosed herein within a period of up to 6 hours, after intercourse, is deemed to be use "after intercourse" as covered by the claims below.

Since a single rinse as disclosed herein can be used either pre-coitus or post-coitus, this type of rinse is also referred to herein as a "peri-coital" rinse. The prefix "peri-" (which appears in words such as perinatal, pericardial, etc.) arises from a Greek word which means around, near, adjacent, etc.

Different formulations and additives may be preferred for pre-coital and post-coital rinses, since they will remain in contact with the genital membranes for different periods of time. As one example, a pre-coital rinse might contain a moisturizer, to counteract the astringent effects of zinc salts, while a post-coital rinse might contain a small concentration of Vitamin E, retinol, and/or other agent(s) that can promote better long-term benefits if allowed to remain in place for a longer period of time.

Any zinc salt that has adequate solubility in water can be evaluated for use as disclosed herein. Candidate organic salts include zinc acetate, zinc lactate, zinc propionate, zinc butyrate, zinc gluconate, zinc formate, zinc glycerate, and zinc glycolate, which are derived from carboxylic acids having a single carboxylic acid group, as well as dicarboxylic acids, such as zinc maleate and zinc malonate. Preferred organic salt candidates include zinc acetate, propionate, and/or lactate (all of which are readily soluble in water).

is gradually depleted of its ions, the zinc gluconate will gradually release more zinc ions.

Inorganic salt candidates (such as zinc chloride or zinc sulfate) can also be evaluated for use as disclosed herein, if desired. However, it should be recognized that they tend to acidify an aqueous mixture, so they may need to be accompanied by a buffer or alkaline neutralizing agent. Inorganic zinc salts as candidate anti-viral additives are discussed in more detail in U.S. Pat. No. 5,980,477 (Kelly, November 1999).

TABLE 1

SOLUBILITY AND IONIC DISSOCIATION (IN WATER) OF VARIOUS ORGANIC SALTS OF ZINC

| Salt | Solubility (grams/liter) | Molecular weight | Molar solubility (moles/liter) | Reported pK values |
|---|---|---|---|---|
| Zinc acetate | 300 (25° C.) | 183.4 | 1.64 | 1.03 |
| Zinc propionate | 320 (15° C.) | 211.5 | 1.51 | 1.01 |
| Zinc butyrate | 107 | 275.6 | 0.4 | 1.00 |
| Zinc formate | 52 (20° C.) | 155.4 | 0.33 | $pK_1 = 0.6, pK_2 = 0.95$ |
| Zinc gluconate | 127 (25° C.) | 455.7 | 0.28 | 1.70 |
| Zinc glycerate (dihydroxypropionate) | NA | 275.6 | NA | 1.80 |
| Zinc glycolate (hydroxyacetate) | NA | 215.5 | NA | 1.92 |
| Zinc lactate | 57 | 279.5 | 0.20 | 1.86 |

Sources:
Cannan and Kibrick, J. Amer. Chem. Soc. 60: 2314 (1938) Sillen and Martell, Stability Constants of Metal Ion Complexes, Spec. Publ. 17 & 25 (The Chemical Society, London, 1964 and 1971) CRC Handbook of Chemistry and Physics, 71st Edition (Boca Raton, FL, 1990) Linke, W. F., ed., Solubility of Inorganic and Metal Organic Compounds, 4th Edition, 1965

Zinc gluconate is also a preferred candidate, since it has a decades-long record of safe internal use; it is less soluble in water, but its solubility can be increased by adding glycine or certain other amino acids to the solution, as described in PCT patent application WO 01/06985 (Godfrey, 2001). Solubility and dissociation data on these and various other organic zinc salts is provided in Table 1. This table has also appeared in various US patents issued to Kelly, as listed above. Additional information on those salts (and certain other salts, as well) is provided in those patents.

Zinc lactate is presumed to be preferred for douche formulations, since there are already large quantities of lactate ions in vaginal fluids, and the vaginal epithelium is well-adapted to handling lactate ions.

If desired, a mixture of several different salts can be used, and may provide various advantages; for example, if a 3% concentration of zinc salt is provided by incorporating 1% zinc acetate, 1% zinc lactate, and 1% zinc gluconate, a balanced blend of three different anions (acetate, lactate, and gluconate ions) is less likely to disrupt various chemical equilibria in the vaginal fluids, if the concentration of each type of ion is reduced by using a blend of all three. Furthermore, since the dissociation kinetics of different salts are different, a balanced blend of all three salts is likely to provide a more sustained and long-lasting plateau of high concentrations of zinc ions. As an example, zinc acetate, which has very high dissociation rates, can release a large initial surge of anti-viral zinc ions. Due to chemical equilibrium factors, this surge of free zinc ions will tend to suppress the early release of even more zinc ions, by zinc lactate. As the surge of zinc ions from zinc acetate gradually subsides and is absorbed, over a span of hours, zinc lactate will begin releasing more zinc ions; and, as the zinc lactate In general, preferred concentrations of zinc salts in anti-viral rinses as disclosed herein are likely to range from about 0.5 to about 5 percent, by weight, depending on which particular salt is used. Higher concentrations can also be used, if desired. In one preferred approach which takes varying individual factors (such as skin sensitivity, perceived degree of risk, etc.) into account, an assortment of different rinses with varying zinc concentrations can be sold, and anyone who wishes to use one will be free to try several different concentrations, and choose one based on their own preferences. This is comparable to sunblocking agents being sold with a range of different "sun protection factors".

It should also be noted that zinc salts that release zinc ions at very high concentrations (such as zinc chloride or sulfate) generally should be used at lower concentrations, while salts that release ions at lower concentrations (such as zinc gluconate) can be used at higher concentrations.

In addition, a peri-coital zinc rinse as disclosed herein can also contain one or more other anti-microbial or other medical agents (such as an anti-fungal agent for preventing or treating vaginal yeast infections), formulated in a manner and concentration which establishes maximum compatibility, efficacy, and synergistic effects when combined and administered along with zinc ions in a non-viscous formulation. Such formulations can be regarded as "zinc boosted" formulations, which are designed to be applied topically to one or more genital surfaces or mucus membranes shortly before or after intercourse. In at least some users, peri-coital formulations of this nature can help promote more regular, consistent, and efficacious use of other active pharmaceutical agents.

Various examples, confirming that water-soluble organic zinc salts did not cause any irritation in human volunteers when added to genital lubricant formulations and used during actual intercourse, are provided in the above-cited US patents issued to Kelly. Those examples are incorporated herein by reference, to support the assertion that zinc salts, when dissolved in aqueous solutions at appropriate concentrations, do not irritate the highly sensitive genital membranes.

Thus, there has been shown and described a new and useful means for creating pre-coital and post-coital rinses containing anti-viral water-soluble zinc salts that, when used shortly before or shortly after intercourse, can reduce the risk of infection by sexually transmitted viruses and possibly other microbes as well. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention, and by the claims which follow.

REFERENCES

Agren, M. S., "Studies on zinc in wound healing," *Acta Dermato-Venereology, Supplement* 154: 1–36 (1990)

Arens, M. and Travis, S., "Zinc salts inactivate clinical isolates of herpes simplex virus in vitro," *J. Clin. Microb.* 38: 1758–1762 (2000)

Bray, T. M. and Bettger, W. J., "The physiological role of zinc as an antioxidant," *Free Radic. Biol. Med.* 8: 281–91 (1990)

Chvapil, M., "New aspects in the biological role of zinc: a stabilizer of macromolecules and biological membranes," *Life Sciences* 13: 1041–1049 (1973)

Chvapil, M., "Effects of zinc on cells and biomembranes," *Med. Clin. North Amer.* 60: 799–812 (1976)

Chvapil et al, "Reaction of vaginal tissue of rabbit and of cheek pouch of hamster to inserted collagen sponges treated with either zinc or copper," *Am. J. Obstet. Gynecol.* 130: 63–70 (1978)

Chvapil et al, "Preliminary testing of the contraceptive collagen sponge," *Obstet. and Gynecol.* 56: 503–506 (1980)

Eby, G. A., and W. W. Halcomb, "Use of topical zinc to prevent recurrent herpes simplex infection: review of literature and suggested protocols," *Medical Hypotheses* 17: 157–165 (1985)

Hennig, B., et al, "Zinc deficiency alters barrier function of cultured porcine endothelial cells," *J. Nutr.* 122:1242–7 (1992)

Kaszuba, M. and Hunt, G. R., "Protection against membrane damage: a $^1$H-NMR investigation of the effect of $Zn^{++}$ and $Ca^{++}$ on the permeability of phospholipid vesicles," *J. Inorg. Biochem.* 40: 217–25 (1990)

Kumel, G., et al, "The mechanism of the anti-herpetic activity of zinc sulphate," *J. Gen. Virol.* 71: 2989–2997 (1990)

Mahadevan, D., et al, "Protection against membrane-mediated cytotoxicity by calcium and zinc," *Am. J. Pathol.* 136: 513–20 (1990)

Novick, S. G., et al, "How does zinc modify the common cold? Clinical observations and implications regarding mechanisms of action," *Medical Hypothesis* 46: 295–302 (1996)

Pasternak, C. A., "Transmembrane communication and disease," *Indian J. Biochem. Biophys.* 27: 363–4 (1990)

Pasternak, C. A., et al, "Membrane damage: Common mechanisms of induction and prevention," *FEMS Microbiol. Immunol.* 5: 83–92 (1992)

Pearce-Pratt, R. and Phillips, D. M., "Studies of adhesion of lymphocytic cells: Implications for sexual transmission of HIV," *Biol. of Reproduction* 48: 431–445 (1993)

Phillips, D. M. and Bourinbaiar, A. S., "Mechanism of HIV spread from lymphocytes to epithelia," *Virology* 186: 261–273 (1992)

Vernazza, P. L., "Genital shedding of HIV-1 despite successful anti-retroviral therapy," *Lancet* 358: 1564 (2001)

Williams, W. L., "New antifertility agents active in the rabbit vaginal contraception method," *Contraception* 22: 659–672 (1980)

Zacharopoulos, V. A., et al, "Lymphocyte-facilitated infection of epithelia by HTLV Type I," *J. Virology* 66: 4601–4605 (1992)

What is claimed is:

1. A composition of matter, comprising an aqueous anti-viral rinsing formulation which is suited for repeated periodic use as a douche by human females, and which is characterized by the absence of any compound that is used as a friction-reducing lubricating agent in conventional genital lubricants, and which contains at least one water-soluble zinc salt at a concentration which releases sufficient quantities of zinc ions to inhibit infectivity of at least one type of sexually transmitted virus if the rinsing formulation is administered as a douche within 15 minutes after ejaculation.

2. The composition of claim 1, wherein the sexually transmitted virus is selected from the group consisting of herpes simplex viruses, human immunodeficiency viruses, hepatitis viruses, and papilloma viruses.

3. The composition of claim 1, wherein at least one zinc salt is selected from the group consisting of zinc acetate, zinc lactate, zinc propionate, zinc butyrate, zinc formate, zinc gluconate, zinc glycerate, zinc glycolate, zinc maleate, and zinc malonate.

4. A composition of matter, comprising an aqueous anti-viral rinsing formulation which is suited for repeated periodic use as an enema, and which is characterized by the absence of any compound that is used as a friction-reducing lubricating agent in conventional genital lubricants, and which contains at least one water-soluble zinc salt at a concentration which releases sufficient quantities of zinc ions to inhibit infectivity of at least one type of sexually transmitted virus if the rinsing formulation is administered as an enema within 15 minutes after ejaculation.

5. The composition of claim 4, wherein the sexually transmitted virus is selected from the group consisting of herpes simplex viruses, human immunodeficiency viruses, hepatitis viruses, and papilloma viruses.

6. The composition of claim 4, wherein at least one zinc salt is selected from the group consisting of zinc acetate, zinc lactate, zinc propionate, zinc butyrate, zinc formate, zinc gluconate, zinc glycerate, zinc glycolate, zinc maleate, and zinc malonate.

7. A method of reducing risk of infection by sexually transmitted viruses, comprising the step of using an aqueous anti-viral rinsing formulation to rinse out a vaginal or rectal cavity, within about one hour prior to commencing intercourse, wherein the aqueous anti-viral rinsing formulation contains at least one water-soluble zinc salt at a concentration which releases sufficient quantities of zinc ions to inhibit infectivity of at least one type of sexually transmitted virus.

8. The method of claim 7, wherein the sexually transmitted virus is selected from the group consisting of herpes simplex viruses, human immunodeficiency viruses, hepatitis viruses, and papilloma viruses.

9. The method of claim 7, wherein at least one zinc salt is selected from the group consisting of zinc acetate, zinc lactate, zinc propionate, zinc butyrate, zinc formate, zinc gluconate, zinc glycerate, zinc glycolate, zinc maleate, and zinc malonate.

10. A method of reducing a risk of infection by sexually transmitted viruses, comprising the step of using an aqueous anti-viral rinsing formulation to rinse out a vaginal or rectal cavity, within about fifteen minutes after completion of intercourse, wherein the aqueous anti-viral rinsing formulation contains at least one water-soluble zinc salt at a concentration which releases sufficient quantities of zinc ions to inhibit infectivity of at least one type of sexually transmitted virus.

11. The method of claim 10, wherein the sexually transmitted virus is selected from the group consisting of herpes simplex viruses, human immunodeficiency viruses, hepatitis viruses, and papilloma viruses.

12. The method of claim 10, wherein at least one zinc salt is selected from the group consisting of zinc acetate, zinc lactate, zinc propionate, zinc butyrate, zinc formate, zinc gluconate, zinc glycerate, zinc glycolate, zinc maleate, and zinc malonate.

* * * * *